United States Patent
Marnfeldt et al.

(10) Patent No.: US 11,607,553 B2
(45) Date of Patent: *Mar. 21, 2023

(54) SIGNALING ERROR CONDITIONS IN AN IMPLANTABLE MEDICAL DEVICE SYSTEM USING SIMPLE CHARGING COIL TELEMETRY

(71) Applicant: Boston Scientific Neuromodulation Corporation, Valencia, CA (US)

(72) Inventors: Goran N. Marnfeldt, Valencia, CA (US); Jordi Parramon, Valencia, CA (US); Christopher Britton Gould, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 199 days.

This patent is subject to a terminal disclaimer.

(21) Appl. No.: 16/951,745

(22) Filed: Nov. 18, 2020

(65) Prior Publication Data
US 2021/0069514 A1    Mar. 11, 2021

Related U.S. Application Data

(63) Continuation of application No. 16/134,783, filed on Sep. 18, 2018, now Pat. No. 10,874,864, which is a continuation of application No. 15/181,584, filed on Jun. 14, 2016, now Pat. No. 10,105,543, which is a continuation of application No. 12/354,406, filed on Jan. 15, 2009, now Pat. No. 9,370,664.

(51) Int. Cl.
*A61N 1/372* (2006.01)
*A61N 1/378* (2006.01)

(52) U.S. Cl.
CPC ........ *A61N 1/3727* (2013.01); *A61N 1/3787* (2013.01); *A61N 1/37217* (2013.01)

(58) Field of Classification Search
CPC ..................... A61N 1/3727; A61N 1/37252
See application file for complete search history.

(56) References Cited

U.S. PATENT DOCUMENTS

| | | |
|---|---|---|
| 3,942,535 A | 3/1976 | Schulman |
| 4,531,523 A | 7/1985 | Anderson |

(Continued)

FOREIGN PATENT DOCUMENTS

| | | |
|---|---|---|
| WO | 2008/004204 | 1/2008 |
| WO | 2008/008281 | 1/2008 |

(Continued)

*Primary Examiner* — Alyssa M Alter
(74) *Attorney, Agent, or Firm* — Lewis & Reese, PLLC

(57) ABSTRACT

The disclosed techniques allow for externalizing errors from an implantable medical device using the device's charging coil, for receipt at an external charger or other external device. Transmission of errors in this manner is particularly useful when telemetry of error codes through a traditional telemetry coil in the implant is not possible, for example, because the error experienced is so fundamental as to preclude use of such traditional means. By externalizing the error via the charging coil, and though the use of robust error modulation circuitry in the implant designed to be generally insensitive to fundamental errors, the external charger can be consulted to understand the failure mode involved, and to take appropriate action.

18 Claims, 13 Drawing Sheets

(56) References Cited

U.S. PATENT DOCUMENTS

| | | |
|---|---|---|
| 5,411,536 A | 5/1995 | Armstrong |
| 5,607,458 A | 3/1997 | Causey, III et al. |
| 5,620,472 A | 4/1997 | Rahbari |
| 5,683,432 A | 11/1997 | Goedeke et al. |
| 5,716,381 A | 2/1998 | Reggiardo |
| 5,755,739 A | 2/1998 | Sun et al. |
| 5,824,022 A | 10/1998 | Zilberman et al. |
| 5,893,049 A | 4/1999 | Reggiardo |
| 6,128,528 A | 10/2000 | Ericksen et al. |
| 6,329,929 B1 | 12/2001 | Weijand et al. |
| 6,389,308 B1 | 5/2002 | Shusterman |
| 6,453,196 B1 | 9/2002 | Von Arx et al. |
| 6,516,227 B1 | 2/2003 | Meadows et al. |
| 6,529,127 B2 | 3/2003 | Townsend et al. |
| 6,532,389 B1 | 3/2003 | Shahandeh |
| 6,560,471 B1 | 5/2003 | Heller et al. |
| 6,622,045 B2 | 9/2003 | Snell et al. |
| 6,745,076 B2 | 6/2004 | Wohlgemuth et al. |
| 6,745,077 B1 | 6/2004 | Griffith et al. |
| 6,772,011 B2 | 8/2004 | Dolgin |
| 6,839,590 B2 | 1/2005 | Waltman |
| 6,959,217 B2 | 10/2005 | DelMain et al. |
| 7,004,924 B1 | 2/2006 | Brugger et al. |
| 7,015,769 B2 | 3/2006 | Schulman et al. |
| 7,138,776 B1 | 11/2006 | Gauthier et al. |
| 7,212,110 B1 * | 5/2007 | Martin .................. A61N 1/3727 607/34 |
| 7,294,127 B2 | 11/2007 | Leung et al. |
| 7,369,635 B2 | 5/2008 | Spital et al. |
| 7,392,092 B2 | 6/2008 | Li et al. |
| 7,406,349 B2 | 7/2008 | Seeberger et al. |
| 7,457,669 B2 | 11/2008 | Katoozi et al. |
| 7,481,763 B2 | 1/2009 | Hassler, Jr. et al. |
| 9,370,664 B2 * | 6/2016 | Marnfeldt .......... A61N 1/37217 |
| 10,105,543 B2 * | 10/2018 | Marnfeldt ............ A61N 1/3787 |
| 10,874,864 B2 * | 12/2020 | Marnfeldt ............ A61N 1/3727 |
| 2002/0151875 A1 | 10/2002 | Haller |
| 2003/0114897 A1 | 6/2003 | Von Arx |
| 2004/0019447 A1 | 1/2004 | Shachar |
| 2004/0171921 A1 | 9/2004 | Say et al. |
| 2005/0004460 A1 | 1/2005 | Taylor et al. |
| 2005/0107676 A1 | 5/2005 | Acosta et al. |
| 2005/0277912 A1 | 12/2005 | John |
| 2005/0283208 A1 | 12/2005 | Von Arx et al. |
| 2006/0020188 A1 | 1/2006 | Kamath et al. |
| 2006/0142820 A1 | 6/2006 | Von Arx et al. |
| 2006/0159074 A1 | 7/2006 | Diebold et al. |
| 2006/0195162 A1 | 8/2006 | Von Arx et al. |
| 2006/0206873 A1 | 9/2006 | Argade |
| 2006/0241356 A1 | 10/2006 | Flaherty |
| 2006/0271119 A1 | 11/2006 | Ni et al. |
| 2007/0066916 A1 | 3/2007 | Lemos |
| 2007/0097719 A1 | 5/2007 | Parramon et al. |
| 2007/0112276 A1 | 5/2007 | Simms, Jr. |
| 2008/0004500 A1 | 1/2008 | Cazares et al. |
| 2008/0155359 A1 | 6/2008 | Ginggen et al. |
| 2009/0062879 A1 | 3/2009 | Li et al. |

FOREIGN PATENT DOCUMENTS

| | | |
|---|---|---|
| WO | 2008/060197 | 5/2008 |
| WO | 2008/063626 | 5/2008 |

* cited by examiner

SIGNALING ERROR CONDITIONS IN AN IMPLANTABLE MEDICAL DEVICE SYSTEM USING SIMPLE CHARGING COIL TELEMETRY

CROSS-REFERENCE TO RELATED APPLICATIONS

This is a continuation application of U.S. patent application Ser. No. 16/134,783, filed Sep. 18, 2018 (allowed), which is a continuation application of U.S. patent application Ser. No. 15/181,584, filed Jun. 14, 2016 (now U.S. Pat. No. 10,105,543), which is a continuation application of U.S. patent application Ser. No. 12/354,406, filed Jan. 15, 2009 (now U.S. Pat. No. 9,370,664). These applications are incorporated herein by reference, and priority is claimed to them.

FIELD OF THE INVENTION

The present invention relates to an improved implantable medical device system able to communicate error conditions via a charging coil even when traditional telemetry techniques are not functional.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable medical device system. For example, the disclosed invention can also be used with a Bion™ implantable stimulator, such as is shown in U.S. Patent Publication 2007/0097719, filed Nov. 3, 2005, or with other implantable medical devices.

As shown in FIGS. 1A and 1B, a SCS system typically includes an Implantable Pulse Generator (IPG) 100, which includes a biocompatible device case 30 formed of titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102, 104 couple to the IPG 100 using lead connectors 38a and 38b, which are fixed in a header material 36, which can comprise an epoxy for example.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils are generally present in the IPG 100: a telemetry coil 13 used to transmit/receive data to/from an external controller 12; and a charging coil 18 for charging or recharging the IPG's battery 26 using an external charger 50. The telemetry coil 13 can be mounted within the header 36 of the IPG 100 as shown.

As just noted, an external controller 12, such as a hand-held programmer or a clinician's programmer, is used to send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12.

Wireless data transfer between the IPG 100 and the external controller 12 takes place via inductive coupling. To implement such functionality, both the IPG 100 and the external controller 12 have telemetry coils 13 and 17. Either coil can act as the transmitter or the receiver, thus allowing for two-way communication between the two devices, as explained further below. When data is to be sent between the external controller 12 and the IPG 100, the transmitting coil 17 or 13 is energized with alternating current (AC), which generates a magnetic field 29, which in turn induces a current in the other of coils 17 or 13. The generated magnetic field 29 is typically modulated using a communication protocol, such as a Frequency Shift Keying (FSK) protocol, which is well known in the art. The power used to energize the coil 17 or 13 can come from batteries 76 and 26 within the external controller 12 and IPG 100 respectively. The induced current in the receiving coil can then be demodulated back into the telemetered data signals.

The external charger 50 is used to charge (or recharge) the IPG's battery 26. Similarly to the external controller 12, the coil 17' is energized with an AC current to create a magnetic field 29. This magnetic field 29 induces a current in the charging coil 18 within the IPG 100, which current is rectified to DC levels, and used to recharge the battery 26, as explained further below. The external charger 50 will generally have many of the same basic components as the external controller 12, and therefore is labeled similar element numerals, denoted with prime symbols. However, while sufficient for purposes of this disclosure to view the external controller 12 and charger 50 as having generally similar components, one skilled in the art will realize that external controllers 12 and chargers 50 will have pertinent differences as dictated by their respective functions.

Inductive transmission of data or power can occur transcutaneously, i.e., through the patient's tissue 25, making it particular useful in a medical implantable device system. During the transmission of data or power, the coils 13 and 17, or 18 and 17', preferably lie along a common axis in planes that are parallel. Such an orientation between the coils will generally improve the coupling between them, but deviation from ideal orientations can still result in reliable data or power transfer.

Further details concerning the communication circuitry in the external controller 12, the external charger 50, and the IPG 100 are shown in FIG. 3. As shown, the external controller 12 and the IPG 100 respectively contain modulation and demodulation circuitry coupled to their coils 17 and 13 for communicating data between them. When data 170 is to be sent from the external controller 12 to the IPG 100, the data is modulated (e.g., encoded) using modulation circuitry 120 in the external controller. On the receiving side, this data 170 is demodulated (e.g., decoded) using demodulation circuitry 125 in the IPG 100. Similarly, when data 172 is to be sent from the IPG 100 to the external controller 12, the data is modulated using modulation circuitry 124 in the IPG. On the receiving side, this data 172 is demodulated using demodulation circuitry 121 in the external controller 12. As mentioned above, one modulation protocol operable in the respective modulation and demodulation circuit blocks 120, 121, 124, and 125 is is FSK, and the details of such circuitry are well known.

The external charger 50 likewise has a two-way communication with the IPG 100, although some differences exist due to the fact that communication from the charger 50 to the IPG 100 generally communicates only unmodulated power 174, not modulated data. Communication of such power 174 occurs using charging circuitry 122 to energize coil 17'. As mentioned above, such power 174 is received at the IPG's charging coil 18, and converted to a DC level using a rectifier circuit 132. This rectified power is then sent to the IPG's battery 26, perhaps via charging/protection circuitry 134 that generally monitors and controls the battery charging process.

The IPG 100 can also communicate data 176 back to the external charger 50. Such back telemetry occurs using modulation circuitry 126. Modulation circuitry 126 receives data to be transmitted back to the external charger 50 from the IPG's microcontroller 150, and then uses that data to modulate the impedance of the charging coil 18. In the illustration shown, impedance is modulated via control of a load transistor 130, with the transistor's on-resistance providing the necessary modulation. This change in impedance is reflected back to coil 17' in the external charger 50, which interprets the reflection at demodulation circuitry 123 to recover the transmitted data. This means of transmitting data from the IPG 100 to the external charger 50 is known as Load Shift Keying (LSK), and is useful to communicate data relevant during charging of the battery 26 in the IPG 100, such as the capacity of the battery, whether charging is complete and the external charger can cease, and other pertinent charging variables.

Also depicted in FIG. 3 is error code circuitry 140 useful in identifying particular failure modes in the IPG 100. The error code circuitry 140 monitors various voltages, interrupt signals, or other indicators 141 within the IPG 100. Through application of its logic, error code circuitry 140 generates an error code (usually numeric) corresponding to the particular failure mode. Because these error codes may be of importance to the patient, the patient's clinician, or the manufacturer of the IPG system, they are typically sent as data 172 from the IPG 100 to the external controller 12. Error code circuitry 140 may comprise a portion of the IPG's microprocessor 150, but is shown as a separate block for simplicity. The error code received at the external controller 12 may be sent to the external controller's user interface 74 for interpretation by the patient, clinician, or manufacturer.

Reporting of IPG error codes external to the patient is of great benefit to understanding, and perhaps fixing, problems with an IPG. As regards fixing such errors, particular error codes may suggest a problem with the software or stimulation program operating in the IPG. If such error codes are known, new software or stimulation programs can perhaps be sent to the IPG to fix the error. Even if a particular error is not immediately fixable, reporting of the error codes is still important to provide analysis of the particular failure involved. Such failure may indicate, for example, whether the IPG 100 can be fixed using extraordinary means (such as through the application of special manufacturer commands), whether the IPG 100 needs to be explanted from the patient, etc. Knowledge of the failure can also assist the manufacture of the IPG system to design a more robust system: without knowledge of particular failure modes, the manufacture may have to embark on complicated and time-consuming failure analysis of the system.

Unfortunately, the inventors have noticed that external reporting of error codes is not always possible. Many times, the inability to report such error codes from the IPG 100 results from failure modes so fundamental that the relevant communication circuitry in the IPG 100—such as the error code circuitry 140, the microcontroller 150, the modulation circuitry 124, etc.—cannot function to communicate the error code to the external controller 12. Such fundamental failure modes may result from improper initialization of the IPG 100. Initialization of the IPG 100 begins with the execution of the microcontroller 150 of "boot up" instructions stored in initialization logic 132. Such an initialization procedure is typically implemented when the IPG 100 recovers from a power down condition, for example, when the battery 26 has become so depleted that the IPG 100 enters a power-down mode or simply can no longer function. The initialization logic 132 may comprise instructions stored within the microcontroller 150, but is shown as a separate block for simplicity. The modulation 124/demodulation 125 circuitry in the IPG 100 may also require initialization, such as tuning or enablement, to function appropriately.

If a fundamental error occurs during initialization, or even after initialization, it may be impossible for the IPG 100 to telemeter error codes outside of the IPG. As a result, the patient, clinician, or manufacture may know nothing about the particular error involved, which inhibits taking any corrective action. The result might be that IPG 100 has to be explanted from the patient, which is painful and inconvenient, and therefore desirable only as a last resort. Such explant is regrettable if the fundamental error could be known, and perhaps fixed. As concerns manufacture of the IPG system, knowledge of fundamental errors greatly assist in failure analysis, which could allow the manufacture to improve the reliably of the IPG system's design. The art of implantable medical devices would benefit from an improved ability to externalize IPG errors, and this disclosure presents solutions.

DETAILED DESCRIPTION

The description that follows relates to use of the invention within a spinal cord stimulation (SCS) system. However, it is to be understood that the invention is not so limited. Rather, the invention may be used with any type of implantable medical device system that could benefit from an improved error condition reporting capability.

Regardless of the embodiment, implementation of the disclosed techniques allow for externalizing errors from an implantable medical device using the device's charging coil, for receipt at an external charger or other external device. Transmission of errors in this manner is particularly useful when telemetry of error codes through a traditional telemetry coil in the implant is not possible, for example, because the error experienced is so fundamental as to preclude use of such traditional means. By externalizing the error via the charging coil, and though the use of robust error modulation circuitry in the implant designed to be generally insensitive to fundamental errors, the external charger can be consulted to understand the failure mode involved, and to take appropriate action.

Figure 3:
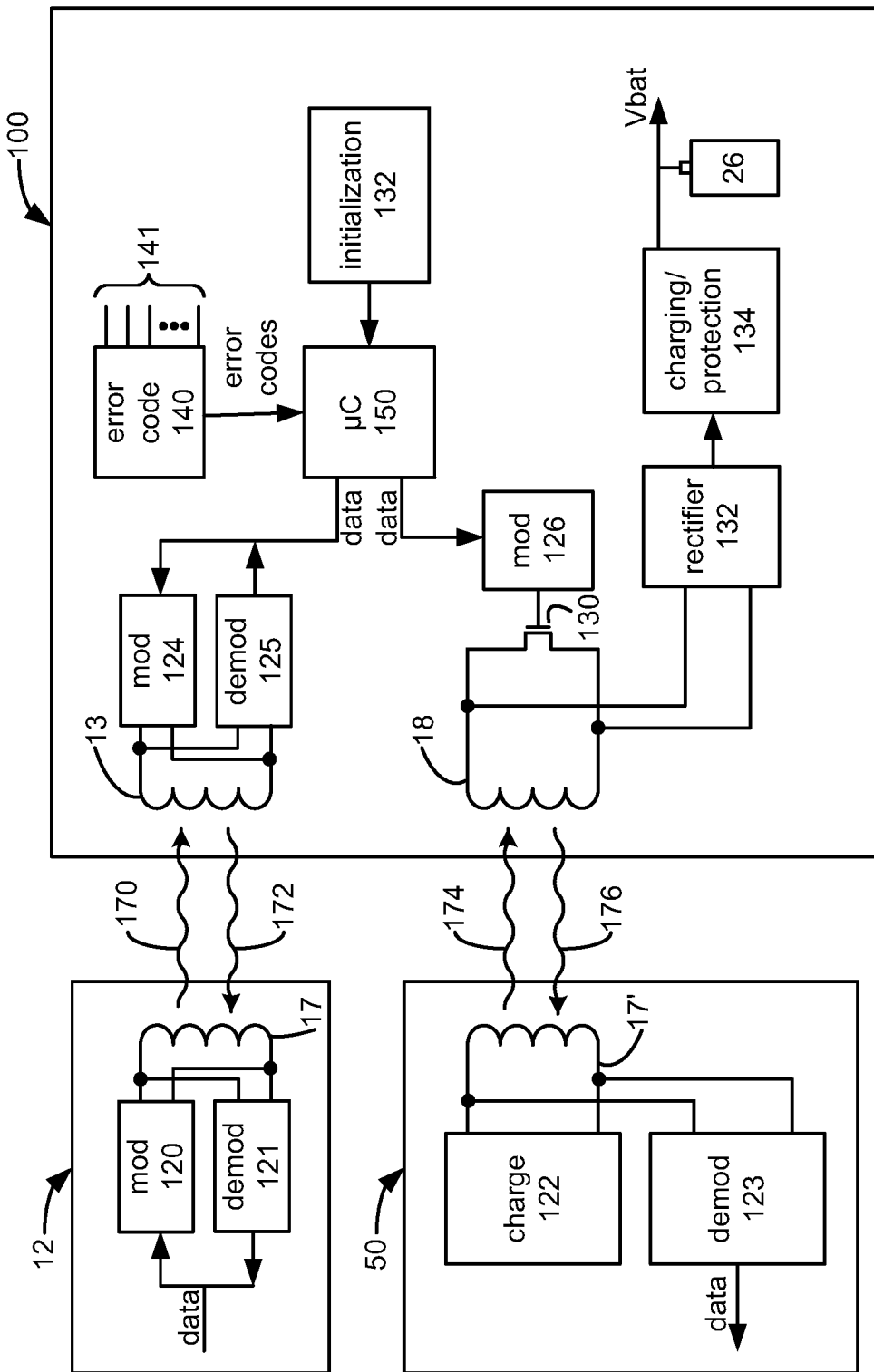
FIG. 3 shows the communication circuitry generally present in the implantable medical device, the external charger, and the external controller.
Figure 4:
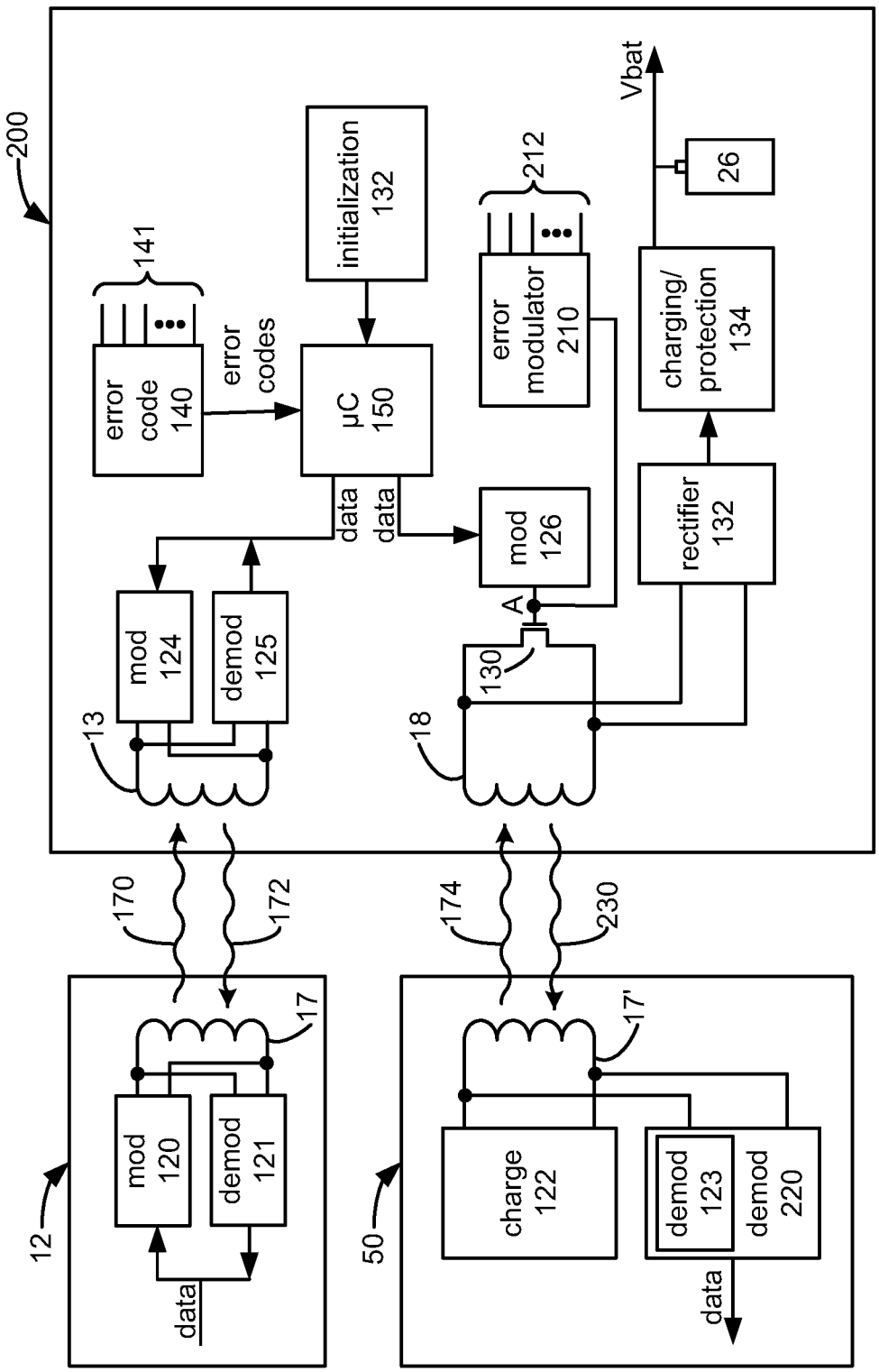
FIGS. 4-6 show a first embodiment of error modulation circuitry for modulating the load transistor of an implant's charging coil to transmit an error sequence indicative of a failure mode in an implantable medical device.

FIG. 4 depicts an embodiment of an improved IPG 200 having a more robust system for communicating errors external to the IPG. As shown, and in comparison to the prior art system of FIG. 3, error modulation circuitry 210 is added to the IPG 200. Like the error code circuitry 140 described earlier, the error modulation circuitry 210 receives various voltages, interrupt signals, or other indicators 212 within the IPG 200. Through its logic, the error modulation circuitry 210 interprets the indicators 212 and modulates the impedance of the charging coil 18, as described further below. The indicators 212 may be the same as, or similar to, the indicators 141 used in conjunction with the error code circuitry 140 already present in the IPG 200. Alternatively, because the error modulator circuitry 210 may concern itself with the transmission of only fundamental errors of the type that prevent communication of the error codes by traditional means using telemetry coil 13, indicators 212 may inform concerning only such fundamental errors. Further, indicators 212 may specifically indicate failures in the initialization logic 132, the microcontroller 150, the modulator circuitry 124, i.e., circuitry that would be required to transmit a failure mode via telemetry coil 13 by traditional means.

To briefly review the prior art discussed in the Background, error codes generated by error code circuitry 140 are traditionally broadcast as data from the LPG's telemetry coil 13 to the external controller 12. By contrast, the error modulator 210 broadcasts error data to the external charger 50 instead of the external controller 12. Such back telemetry of error data preferably bypasses the traditional modulator 126 used to communicate with the external charger 50. Accordingly, the error modulator 210 connects directly to the load transistor 130 used to modulate the impedance of the charging coil 18. Using such modulation, errors determined by error modulator 210 can be sent to the external charger 50 where they are decoded at demodulator 220. Demodulator 220 in the external charger 50 will also decode normal back telemetry from coil 18 (data from modulator 126 reporting on battery status during charging for example), and therefore will include demodulator 123 of the prior art (FIG. 3), which may be maintained as a distinct circuit block from other portions of the demodulator 220 involved in decoding the errors transmitted by the error modulator 210.

Because it relies on reflections, telemetry from the IPG 200 to the external charger 50 is passive and relies on the magnetic field provided by the external charger to operate. As a result, the external charger 50 must be active to receive transmissions from both the modulator 126 (e.g., status data) and the error modulator 210 (error data). However, in a preferred implementation, when a fundamental error occurs as determined by the error modulator 210, modulation of the charging coil 18 begins regardless whether the external charger 50 is active. In other words, error modulator 210 starts continuously modulating the impedance of the charging coil 18 to transmit (e.g., reflect) the detected fundamental error even if the external charger 50 is not yet active to receive the error. In this way, it is assured that when the external charger 50 is eventually activated, it will immediately start receiving the error determined by the error modulator 210.

Error modulator 210 is preferably designed to be robust to minimize the possibility that it will be affected by fundamental errors, such as those resulting from improper initialization of the IPG 200. In its simplest form, error modulator 210 comprises logic circuitry. In some embodiments, the error modulator 210 depends only upon battery power (Vbat) for proper operation, and thus is not dependent on the initialization logic 132, the microcontroller 150, or the modulator circuitry 124, i.e., those circuit blocks traditionally used to transmit error code to the external controller 12. This keeps problems in those circuit blocks from affecting operation of the error modulator 210. In other embodiments, the error modulator 210 can receive data from the microcontroller 150, or can comprise a part of the microcontroller.

Figures 1A, 1B:
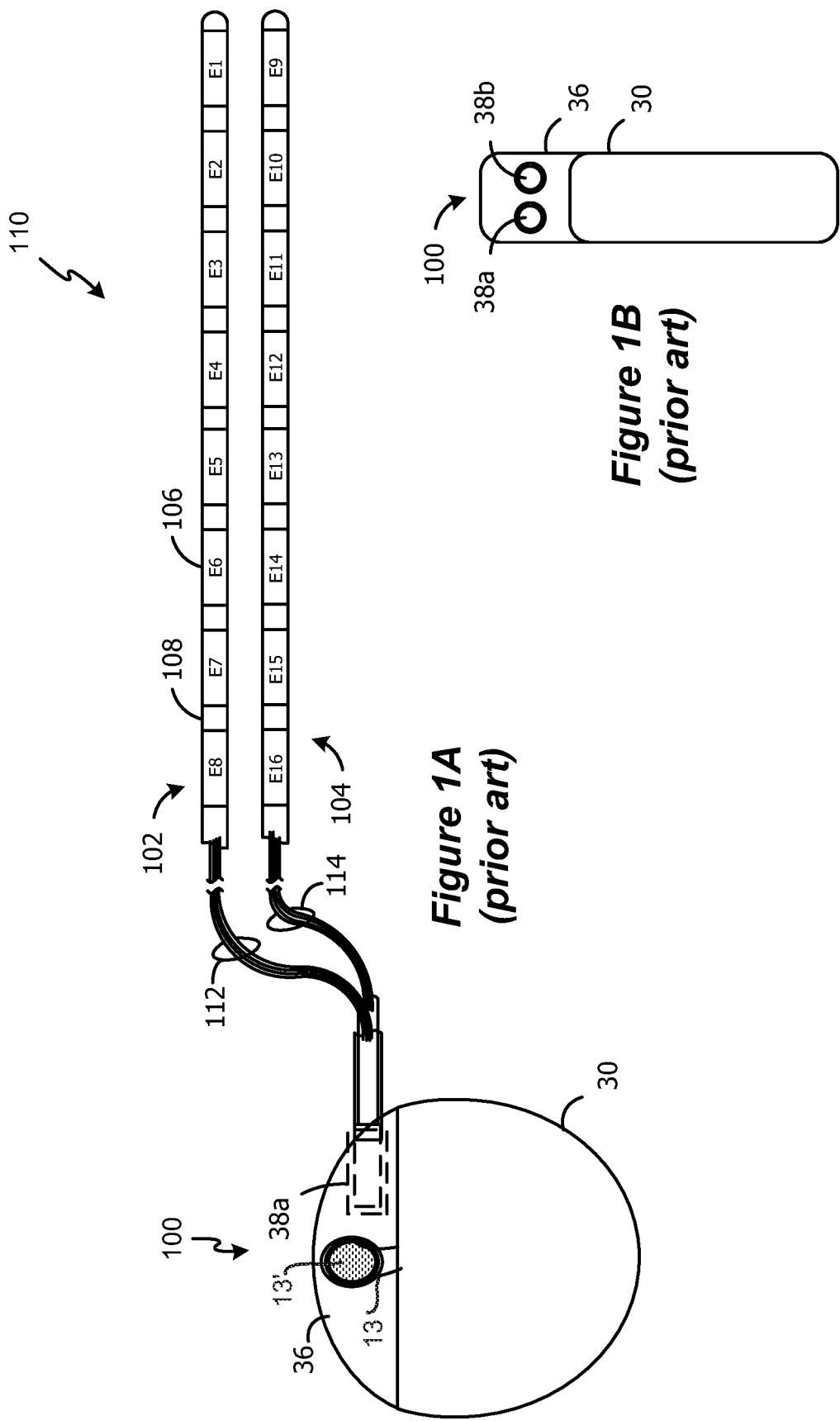
FIGS. 1A and 1B show an implantable medical device, and the manner in which an electrode array is coupled to the IPG in accordance with the prior art.
Figure 2:
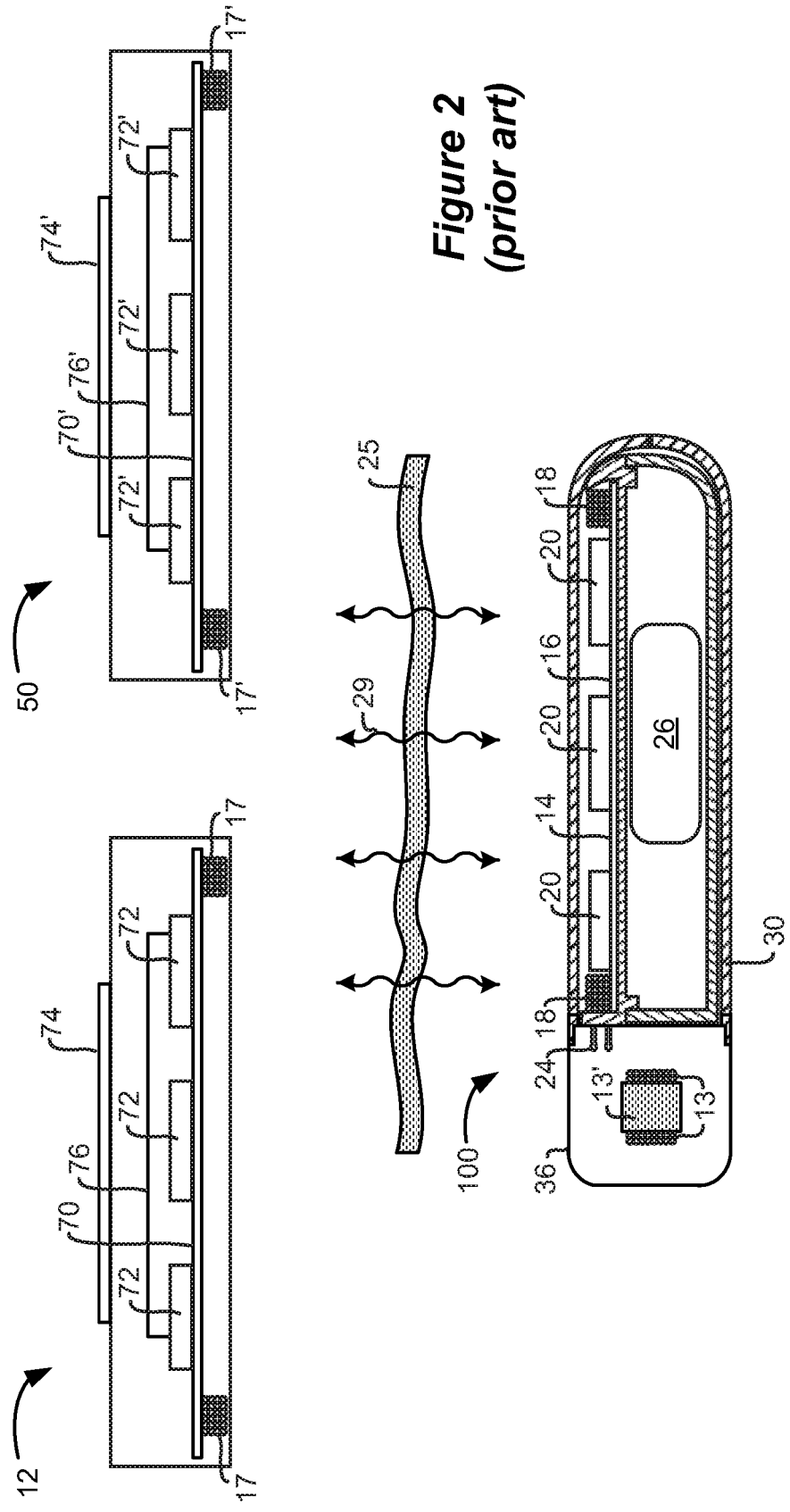
FIG. 2 shows the relation between the implantable medical device, an external controller, and an external charger.

When a fundamental error occurs, the patient, clinician, or manufacturer in accordance with the disclosed technique will eventually activate the external charger 50 to discern the failure mode involved. For example, suppose the IPG 200 has encountered a fundamental error, perhaps because the IPG 200 has failed to initialize as described earlier. During such time, both the error code circuitry 140 and the error modulator 210 have been receiving their respective indicators 141 and 212. However, if the error is fundamental, it may not be possible to transmit the error code from the telemetry coil 13 in the IPG: for example, the microcontroller 150 or the modulator circuitry 124 may not have been properly initialized or may be suffering from other failures. The patient, clinician, or manufacturer, upon noticing a failure, will normally first consult the external controller 12 to see if the error code has been reported. (Indeed, if one is already using the external controller 12, for example for the specific purpose of initializing the IPG 200, the external controller 12 may already be "in hand"). When it is noticed at the external controller's user interface 74 (FIG. 2) that the error code is not received at the external controller 12, the patient, clinician, or manufacturer can now activate the external charger 50 to detect the error being transmitted by the error modulator 210, and if possible, take appropriate corrective action.

Figure 5:
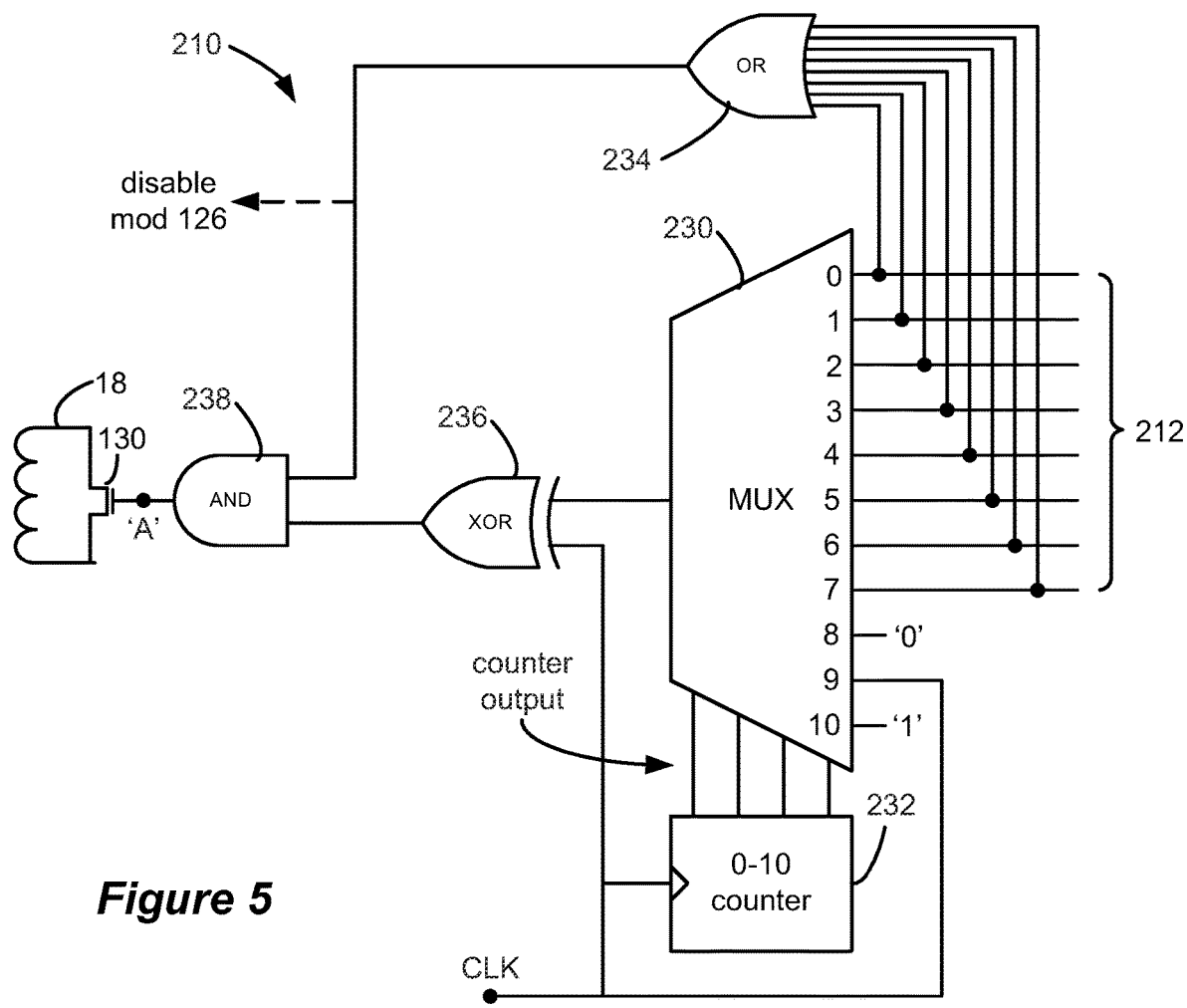
Figure 5:
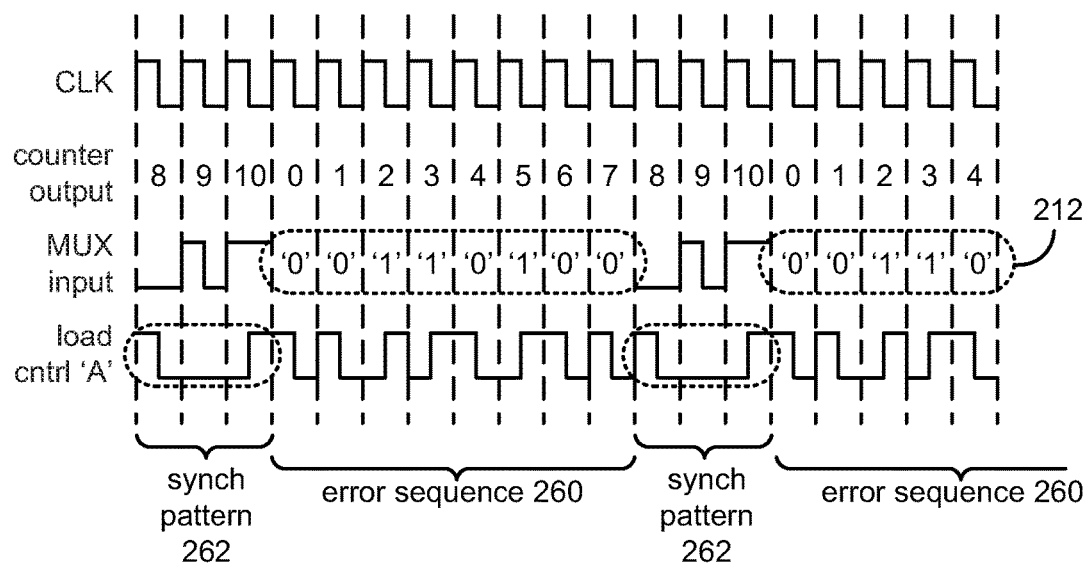

As noted above, error modulator 210 is made as simple as possible, and may be implementable as logic gates powered by the battery 26 requiring no initialization or enablement to function. One embodiment of the error modulator 210 is shown in FIG. 5. Error indicators 212 are input to a multiplexer (mux) 230, which chooses one of inputs 0-10 in accordance with the status of counter 232. In the illustrated example, inputs 0-7 comprise the error indicators 212, which allows the error modulator 210 to output 256 ($2^8$) different error sequences 260. Inputs 8-10 to the mux 230 are used to generate a synchronization pattern 262 as explained further below. The counter 232 outputs a value from 0 ('0000') to 10 ('1010') on a 4-bit binary bus to choose the corresponding mux input. The counter 232 is incremented by a clock signal, CLK, which can comprise the master clock signal for the IPG 200, a crystal oscillator, an inverter loop, a delay- or phase-locked loop, or any other well-known clock generation circuitry. Once the maximum value of the counter (10 in this example) is reached, the counter resets back to 0 to continue counting.

The error sequence 260 in the illustrated example is Manchester encoded using exclusive OR (XOR) gate 236, which XORs the chosen mux input with one period of the clock signal. If the chosen input comprises a '1', the output of XOR gate 236 comprises a rising transition which is inverse to the clock period; conversely, if the chosen input comprises a '0', the output comprises a falling transition, which matches the clock period. Thus, logic '1' and '0's are represented respectively by rising or falling transitions, consistent with an application of Manchester encoding.

As noted earlier, the error modulator 210 preferably operates to broadcast detected errors from the charging coil 18 in the IPG 200 any time an error is detected, i.e., any time one of the indicators 212 is asserted. Such broadcasting preferably occurs even when the external charger 50 is not active, and is thus not yet able to receive the reflected error transmission. To determine whether an error is present, all of the indicators 212 are ORed at OR gate 234, such that the output of OR gate 234 is '1' when any indicator 212 comprises a '1'. This OR gate output is input to an AND gate 238, whose other input comprises the Manchester encoded error data from XOR gate 236. If none of the indicators is '1', the output of OR gate 234 will be '0', and AND gate 238 will necessarily output a '0' to load control node A. This prevents needless toggling of the load transistor 130 when no error is indicated, which saves power. By contrast, if any indicator is '1', the OR gate outputs a '1,' and the Manchester encoded data is passed by AND gate 238 to load control node A. For example, FIG. 5 shows the assertion of three indicators, namely inputs 2, 3, and 5 to the mux 230. The result at node A is modulation of the load transistor 130 with a '00110100' pattern, where each sequential state comprises rising or falling transitions as discussed earlier, and as shown in the timing diagram of FIG. 5. Note that when the output of the OR gate 234 indicates a failure mode, that failure indication can be sent to the back telemetry modulator 126 (FIG. 4) to disable operation of that circuit, as shown in dotted lines in FIG. 5. In other words, an error assertion by error modulator 210 is given priority access to charger coil 18 over normal back telemetry communications (e.g., battery status) desired by modulator 126.

Error transmission preferably repeats so long as one of the indicators 212 continues to be active. To demark the beginning and end of the error sequence 260, a unique synchronization pattern 262 can be used, as illustrated in FIG. 5. In the depicted embodiment, the synchronization pattern 262 is generated by holding mux input 8 to a '0', input 10 to a '1', and by providing the clock to input 9. When the counter 232 selects mux input 8, a falling edge is created at node A. When selected, input 9, the clock signal, is XORed to itself, thus providing a non-transitioning, low output at node A. Input 10, when selected, provides a rising transition at node A. The overall effect is the creation of a unique synchronization pattern 262 having a low condition lasting longer than a clock period, which condition cannot represent a valid data state in the Manchester-encoded error sequence 260. Detection of this unique pattern 262 at the demodulation circuitry 220 in the external charger 50 (FIG. 4) allows the external charger 50 to understand when the error sequence 260 starts and stops. Like the error sequence 260, the synch pattern 262 will not be needlessly generated at load control node A if no error indicator 212 has been asserted.

Figure 6:
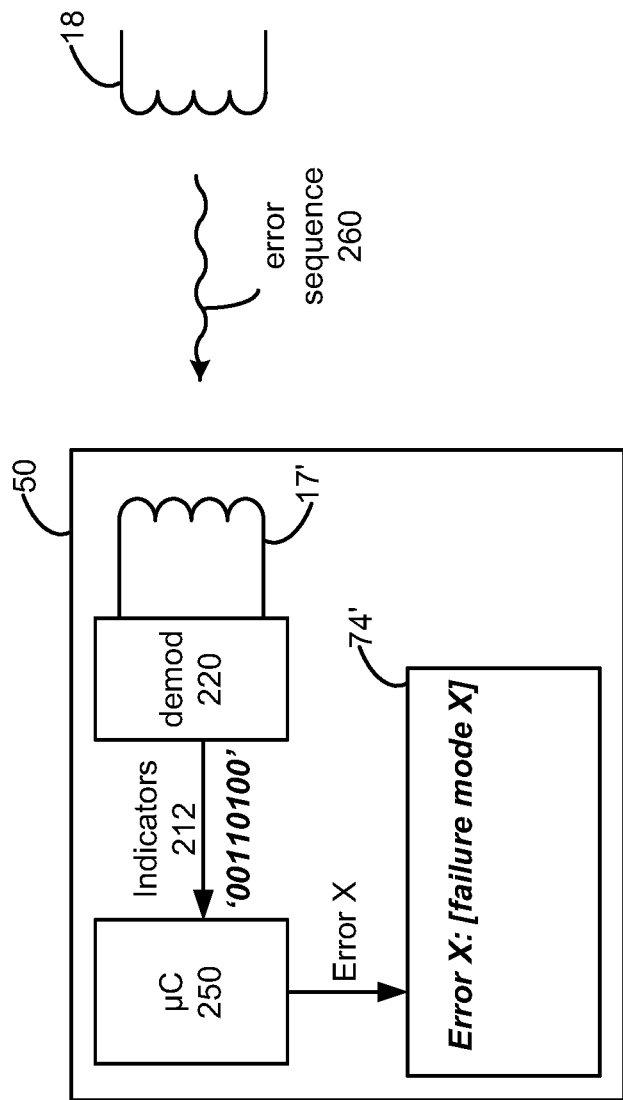

Once the error sequence 260 is received at coil 17' of the external charger 50, as shown in FIG. 6, it is demodulated 220 to recover the sequence of indicators 212. If the external charger 50 has its own microcontroller 250 as is typical, the indicators 212 can then be decoded at the microcontroller to provide information about the error to the user interface 74' (e.g., screen) of the external charger. Because eight indicator bits are used in the illustrated example, 256 different failure modes [Error 0-Error 255] can be indicated, and can be indicated at the user interface 74'. If helpful, a short textual description of the failure (e.g., "[failure mode X]") can also be displayed along with error number, which such textual descriptions being stored in the memory of the microcontroller 250, or other memory accessible to the microcontroller.

The circuitry comprising the error modulator 210 as shown in FIG. 5 generally needs only the voltage of battery 26, Vbat (or buffered or regulated versions thereof) and a clock source (which may or may not comprise part of the error modulator 210) to function. Such circuitry, typically implemented in CMOS, can run at voltages of 2V or less, and thus can operate even when the battery power is insufficient to allow full operation of the IPG 200. The error modulator 210 could even be powered by the output of rectifier 132 and thus be independent of battery voltage altogether, which would allow reporting of error conditions relating to low battery power.

Figure 7:
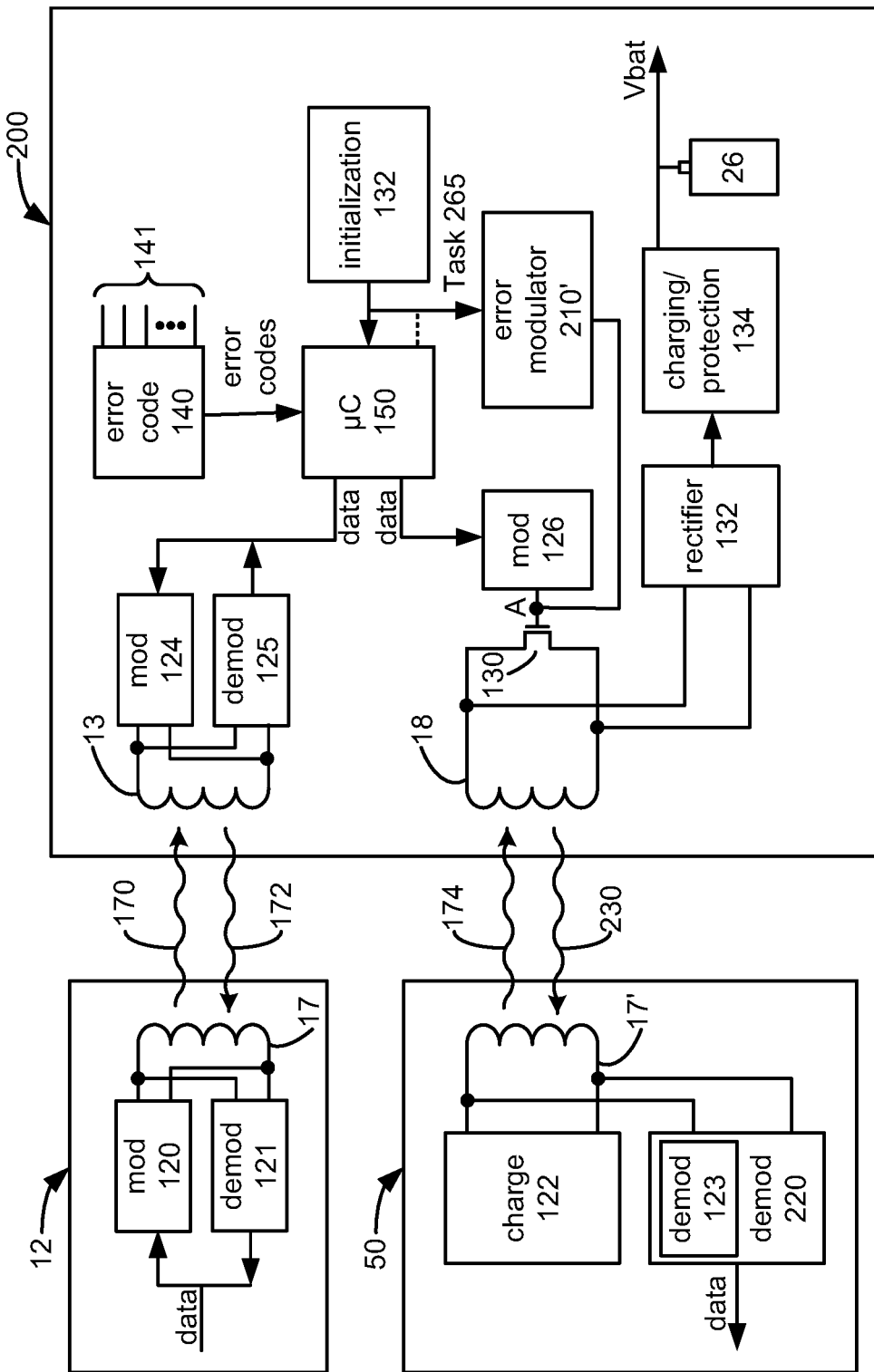
FIGS. 7-9 show a second embodiment of error modulation circuitry for modulating the load transistor of an implant's charging coil to transmit a continuous frequency indicative of a failure mode in the implant.

FIG. 7 illustrates another embodiment of an error modulator 210' for sending error indications to the external charger 50. In this application, the error modulator 210' converts a task indicator 265 to a modulation frequency for the load transistor 130. The task indicator 265 can comprise a particular initialization task for example, and hence can receive input directly from the initialization logic 132 as shown. Alternatively, the task indicator 265 can comprise instructions provided by the microcontroller 150, as shown in the dotted line.

Figure 8:
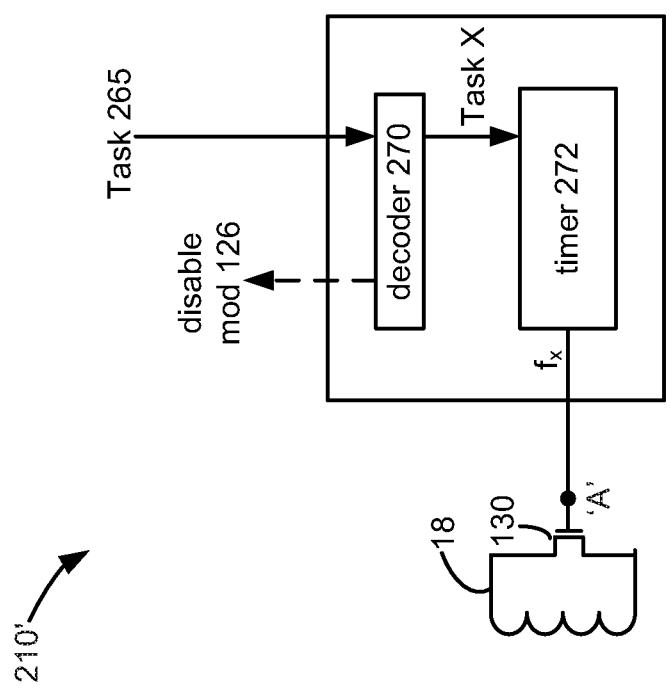

Further details concerning the error modulator 210' are shown in FIG. 8. Task indicator 265, which may be carried on a serial or parallel bus, is first decoded (270) if necessary into the particular task X at hand. Once a task requiring activation of the load transistor 130 is identified, a disable signal can be sent to the standard charging coil 18 modulator 126 (FIG. 4) to allow the error modulator 210' priority to the coil, as discussed previously.

Once the particular task X is known, it is input to programmable timer circuitry 272 capable of generating a clock signal of a particular frequency, $f_x$. Timer circuitry 272 can comprise a crystal oscillator, a voltage controlled oscillator, a phase- or delay-locked loop, or any other well known adjustable clock generation circuitry. Timer circuitry 272 is often present in the microprocessor 150 used in the IPG 200, and thus additionally circuitry beyond the microcontroller 150 may not be required to implement the error modulator 210'. In any event, the error modulator 210' and its sub-circuits are shown separately in the Figures for convenience.

Figure 9:
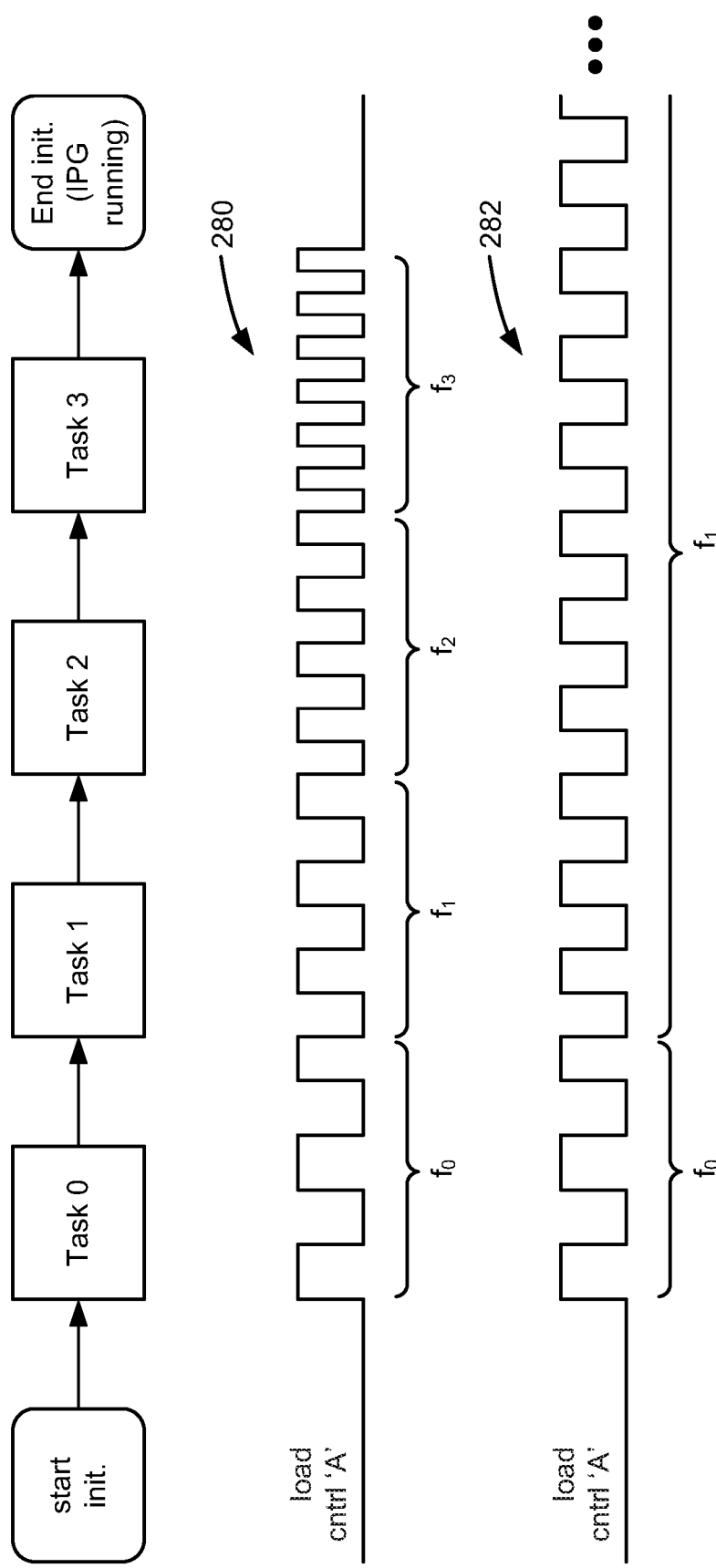

FIG. 9 illustrates the operation of the error modulator 210'. It is assumed in this example that IPG initialization requires the ordered performance of four tasks, Task 0-Task 3, to render the IPG 20 fit for operation. The operation of the error modulator 210' is illustrated by two scenarios 280 and 282. In scenario 280, no fundamental error is experienced. Thus, once Task 0 is indicated, the error modulator outputs a clock signal at load controller node A of $f_0$. That output continues uninterrupted until Task 1 is indicated, at which time the output is changed to $f_1$, etc. This continues until all tasks are completed, at which time the timer 272 ceases generation of the clock signal. At this time, the disable signal to normal charging coil modulator 126 can be re-enabled.

Scenario 282 illustrates the operation of the error modulation circuitry 210' when a fundamental error occurs. Specifically illustrated is the example in which the IPG 200 experiences an error in the performance of Task 1. As before, the process begins with the indication of Task 0 and its corresponding output of $f_0$, followed by the indication of Task 1 and its corresponding output of $f_1$. However, because of a fundamental failure during the performance of Task 1, the IPG 200 ceases execution, or "hangs up." As a result, Task 2 is never indicated, and the error modulator 210' continues to output frequency $f_1$ indefinitely, providing a simple indication of error.

This frequency $f_1$ is then detectable at the demodulator 220 (FIG. 4) in the external charger 50 the next time the external charger is operated and capable of receiving impedance reflections from the IPG's charging coil 18. As before, the patient, clinician, or manufacturer can know to operate the external charger 50 when it appears evident that the IPG 200 is not functioning properly, perhaps after first (unsuccessfully) checking the error on the external controller 12.

Errors are thus indicated using error modulator 210' as a single frequency, with $f_x$ indicating error x (or failure mode x). As indicated earlier in FIG. 6, such error number and/or failure mode by be presented on the user interface 74' of the external charger 50. Because errors are indicated by only a single frequency, the number of errors transmittable from the IPG 200 to the external charger 50 are more limited than in the multi-bit example of FIGS. 4-6. The number of useable error frequencies depends on the number of frequencies the timer 272 is capable of outputting, the resonant frequencies of the charging coils 18 and 17' in the IPG 200 and external charger respectively, and the ability of the demodulator 220 to decode such frequencies at demodulator 220. However, because the number of tasks the IPG 200 must perform upon initialization may be limited, use of a limited number of error frequencies may be suitable.

Figure 10:
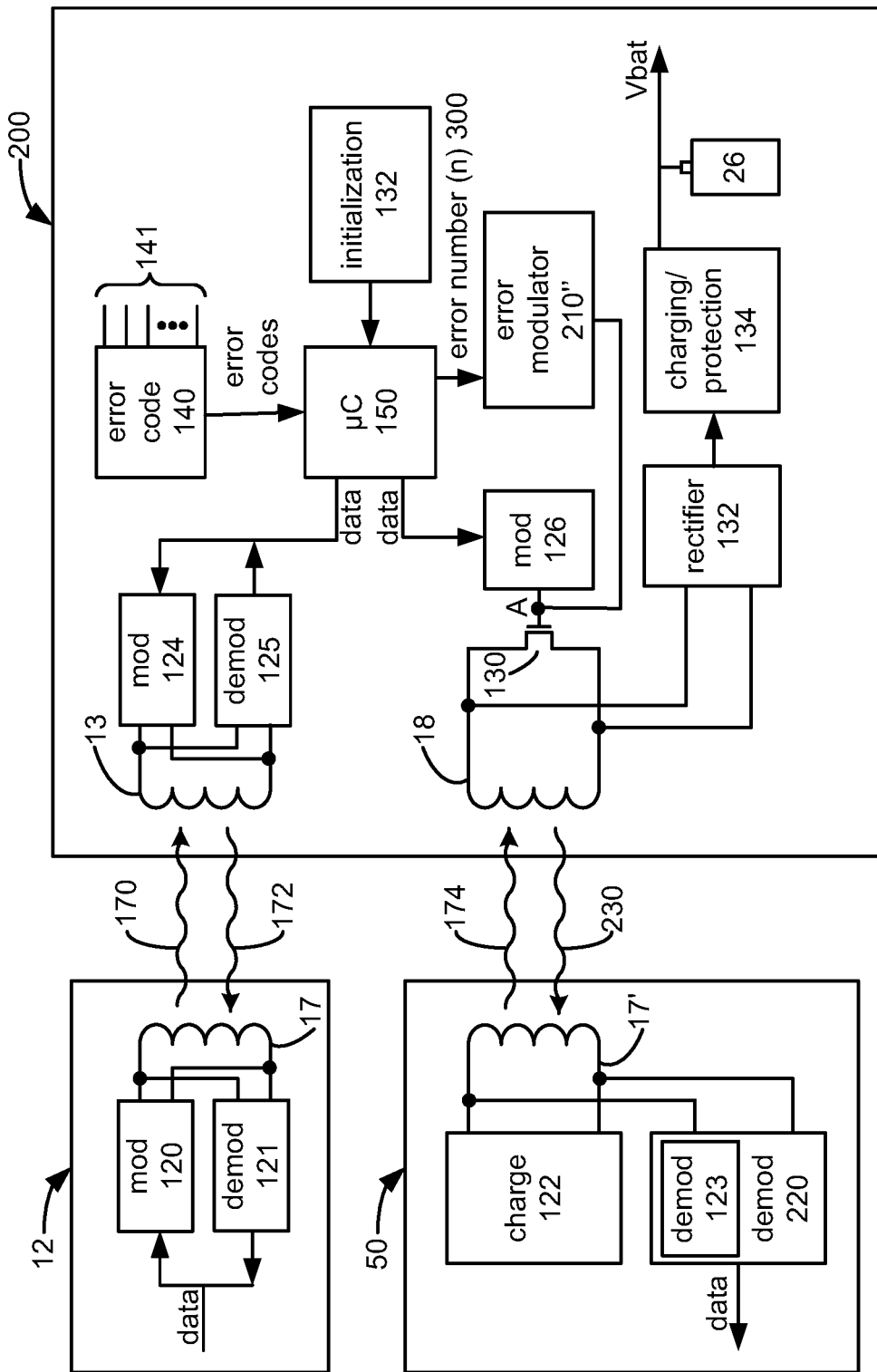
FIG. 10-13 show a third embodiment of error modulation circuitry for modulating the load transistor of an implant's charging coil to transmit a continuous frequency indicative of a failure mode in the implant.

FIG. 10 indicates another embodiment for the error modulator 210", and its basic circuitry and operation are explained with reference to FIGS. 11-13. As with error modulator 210' (FIGS. 7-9), error modulator 210" indicates an error at charging coil 18 by modulating the load transistor 130 with a single continuously-broadcast frequency. Thus, once again, the external charger interprets the error condition by assessing the reflection frequency, $f_x$. However, in FIGS. 10-13, the error modulator 210" uses different circuitry to accomplish this result.

In this embodiment, an error is determined and assigned an error number 300, designated as n. This error number may be derived in the microcontroller 150 and sent to the error modulator 210" as shown in FIG. 10. Once again, the error modulator 210" can comprise stand-alone circuitry, or may comprise a portion of the microcontroller 150.

The error number 300, n, is used generate a particular frequency for the load control node A. One method of doing so is shown with reference to the circuitry in FIG. 11. As shown, the error number, n, is entered into a decrement counter 320, which is clocked using the IPG 200's system clock for example. As the counter 320 decrements, it eventually reaches a value of zero, at which point, the counter's output Q goes high. This output is sent to the T input of a T flip flop 330, which is again clocked, and which toggles its output Q (i.e., changes its logic state) when input T is asserted. This toggled output generates a clock signal at load control node A with a frequency $f_x$ that is a function of the error number n 300 entered into the counter 320.

Figure 11:
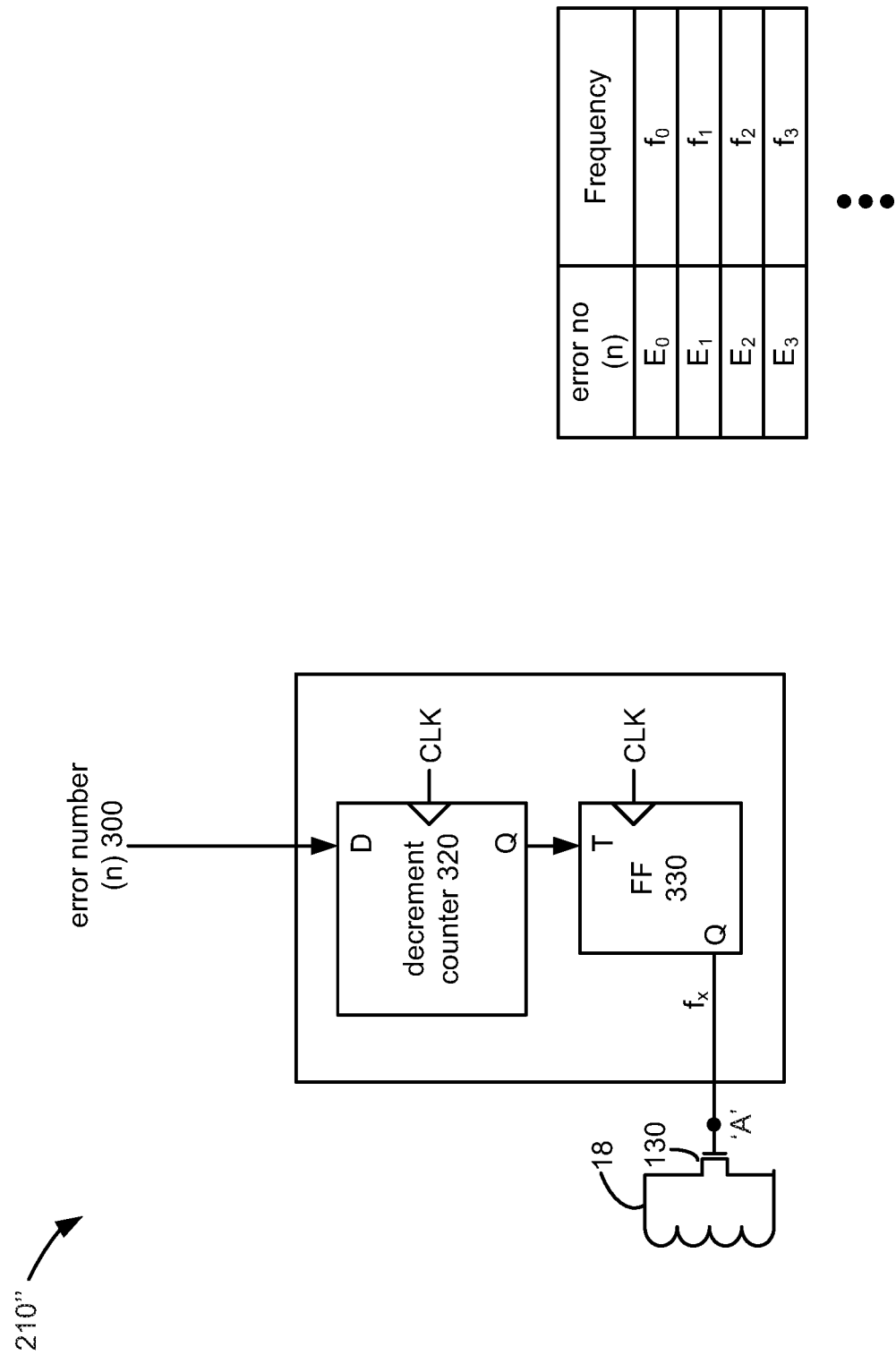
Figure 12:
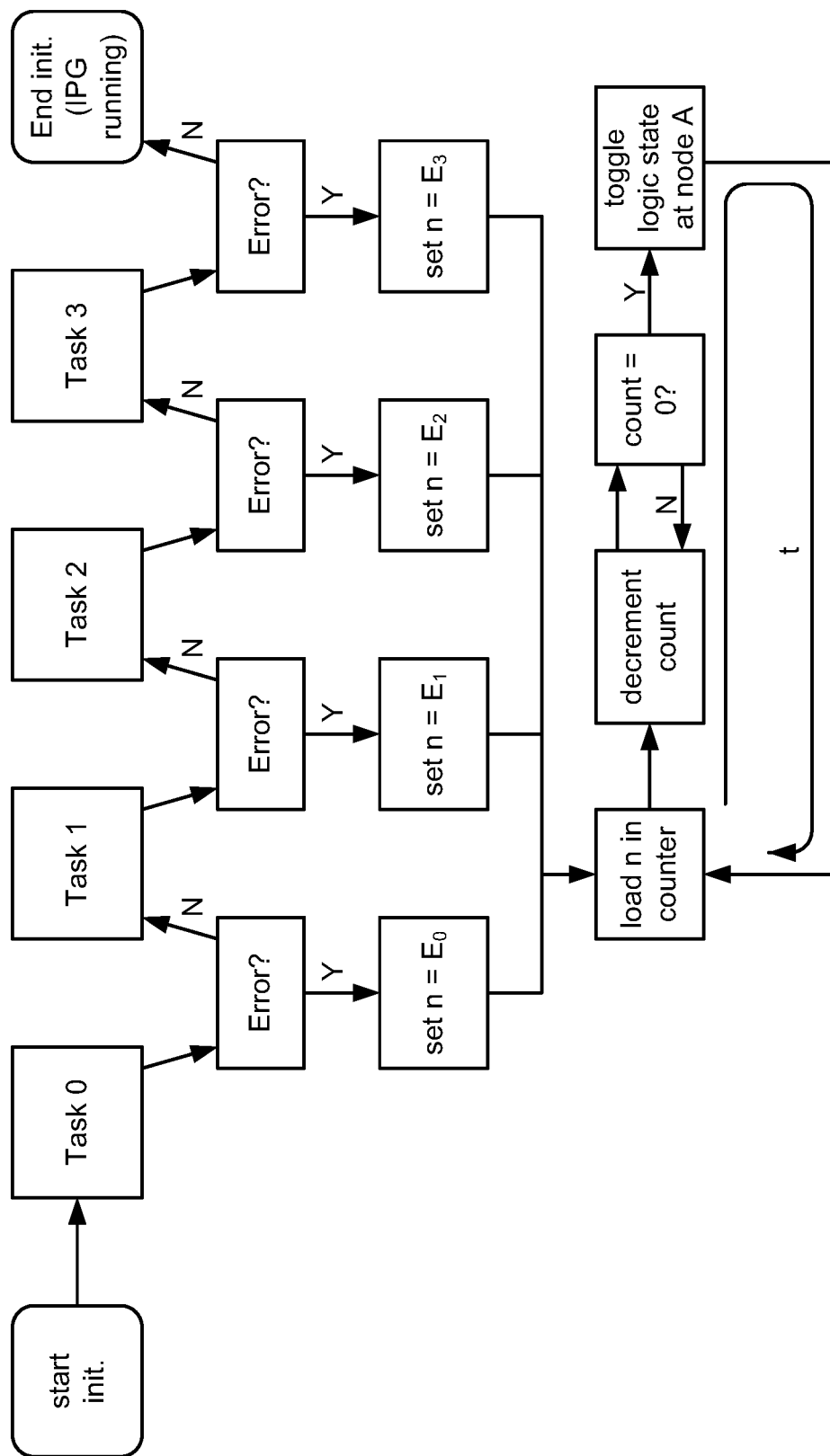

This relationship between frequency and error number is illustrated in FIG. 12, which describes the operation of the error modulator 210" of FIG. 11. As with error modulator 210' (FIGS. 7-9), error modulator 210' is designed to proceed through a number of initialization tasks, and four such tasks are illustrated in FIG. 12. If no error is encountered at a given step, the routine proceeds to the next step as shown, and the load controlled node A for the load transistor 130 is left unmodulated. However, if an error is encountered at any one of these tasks, the microcontroller 150 or other logic issues an error number (n=$E_x$) corresponding to the particular task (Task X) at issue. This error number, n=$E_x$, is loaded into the counter 320, which begins to decrement. When the count in the counter 320 equals zero, the logic state at load control node A is toggled by T flip flop 330 as discussed earlier. The counter 320 is then reset with the error number Ex, and the process repeats to once again toggle the logic state of node A.

Figure 13:
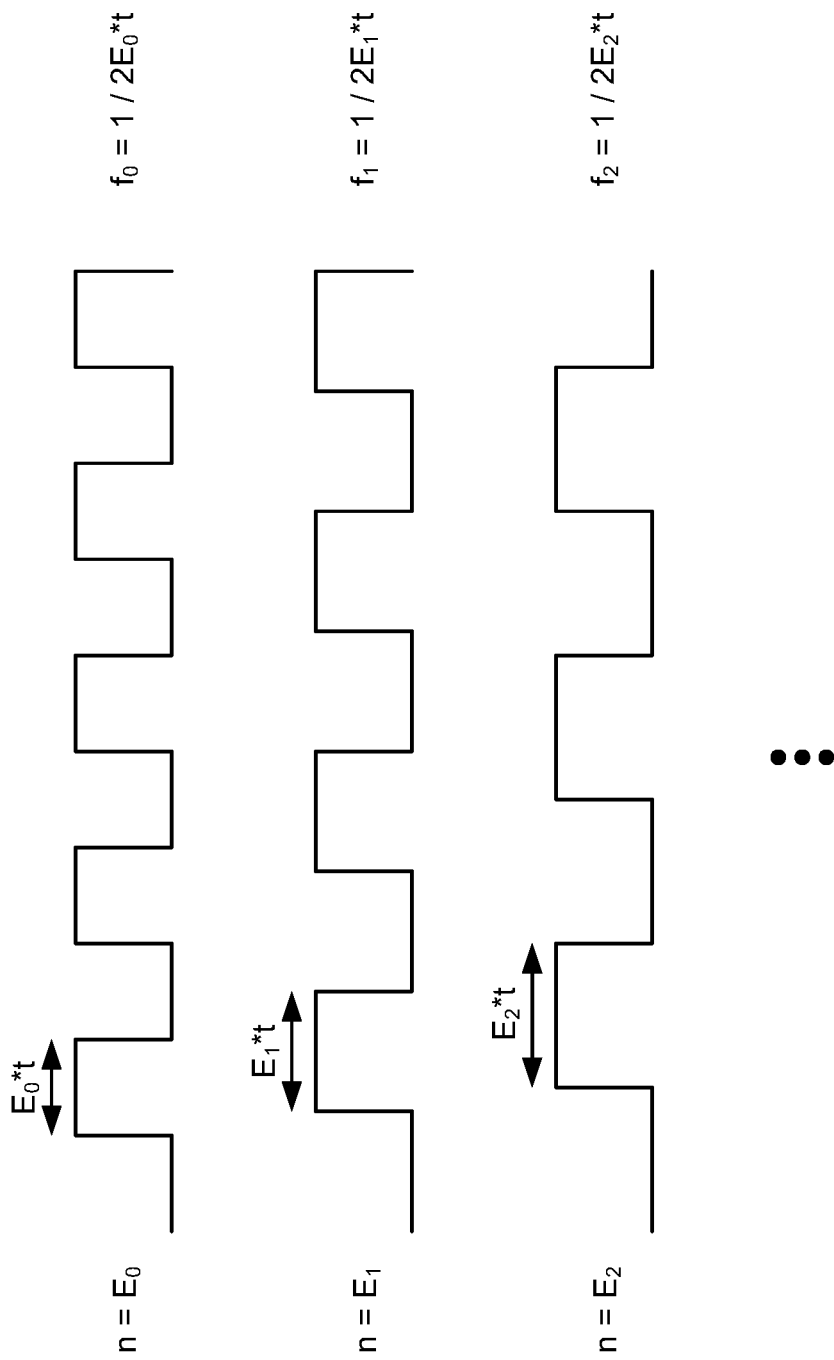

The effect of this, shown in FIG. 13, is the generation of a clock signal having a half period equal to the error number $E_x$ times the length of time it takes to decrement the counter 320, denoted at 't' in FIG. 12. Each error number, $E_x$, thus corresponds to a frequency, $f_x=1/(2*E_x*t)$, which frequency is used to toggle the load transistor 130, and is thus transmitted to the external charger 50. As with the frequency generated by the error modulator 210' of FIGS. 7-9, the error modulator 210" of FIGS. 10-13 preferably continuously broadcasts the frequency corresponding to the error, $E_x$, to allow the external charger 50 to receive and decode this frequency, and correlate it to a particular error or failure mode, at a first available opportunity.

The enclosed embodiments illustrate the sending of error information from an implant's charging coil (i.e., the coil that receives power) to an external charger (i.e., the device that provides that power) as opposed to an external controller (e.g., the device that among other things sends a therapeutic program to the implant to control its therapeutic operation). However, it is not necessary that the external controller 12 and the external charger 50 be separate devices. Thus, sending error indicators from the implant's charger coil pursuant to the disclosed techniques can be to any external device which also functions to provide power to the implant, even if that device performs other functions.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device, comprising:
   a charging coil configured to receive power from an external charger, rectifier circuitry configured to rectify power received by the charging coil, error modulation circuitry configured to determine whether one of a plurality of errors is present in the implantable medical device and, if so, to communicate an indication of the determined error to the external charger, and a battery, wherein the rectifier circuitry is configured to directly power the error modulation circuitry independent of power in the battery.

2. The device of claim 1, wherein communicating an indication of the determined error comprises modulating an antenna of the implantable medical device.

3. The device of claim 2, wherein the antenna is a coil.

4. The device of claim 2, wherein the modulating the antenna comprises modulating the antenna a one of a plurality of frequencies, wherein each frequency of the plurality of frequencies is unique to a different determined error.

5. The device of claim 2, wherein the error modulation circuitry is directly coupled to a load transistor that is controlled to modulate an impedance of the antenna.

6. The device of claim 1, wherein communicating an indication of the determined error comprises modulating the charging coil.

7. The device of claim 1, wherein the error modulation circuitry is configured to operate at a power level that is below that which is required for full operation of the device.

8. The device of claim 1, wherein the error modulation circuitry is configured to operate when the battery is dead.

9. A system, comprising:
an implantable medical device; and
an external charger device,
wherein the implantable medical device comprises:
a charging coil configured to receive power from the external charger device,
rectifier circuitry configured to rectify power received by the charging coil,
error modulation circuitry configured to determine whether one of a plurality of errors is present in the implantable medical device and, if so, to communicate an indication of the determined error to the external charger, and
a battery,
wherein the rectifier circuitry is configured to directly power the error modulation circuitry independent of power in the battery.

10. The system of claim 9, wherein communicating an indication of the determined error comprises modulating an antenna of the implantable medical device.

11. The system of claim 10, wherein the antenna is a coil.

12. The system of claim 10, wherein the modulating the antenna comprises modulating the antenna a one of a plurality of frequencies, wherein each frequency of the plurality of frequencies is unique to a different determined error.

13. The system of claim 10, wherein the error modulation circuitry is directly coupled to a load transistor that is controlled to modulate an impedance of the antenna.

14. The system of claim 9, wherein communicating an indication of the determined error comprises modulating the charging coil.

15. The system of claim 9, wherein the error modulation circuitry is configured to operate at a power level that is below that which is required for full operation of the device.

16. The system of claim 9, wherein the error modulation circuitry is configured to operate when the battery is dead.

17. The system of claim 9, wherein the external charger comprises a screen configured to indicate the determined error to a person.

18. The system of claim 9, wherein the external device is configured to receive the indications of the plurality of errors only when transmitting power to the implantable medical device.

* * * * *